United States Patent [19]

Terashima et al.

[11] Patent Number: 4,495,103
[45] Date of Patent: Jan. 22, 1985

[54] PREPARATION OF OPTICALLY ACTIVE 4-DEMETHOXYDAUNOMYCINONE

[75] Inventors: Shiro Terashima, Tokyo; Katsumi Tamoto, Funabashi; Masamichi Sugimori, Tokyo, all of Japan

[73] Assignee: Sumitomo Chemical Company, Ltd., Osaka, Japan

[21] Appl. No.: 471,338

[22] Filed: Mar. 2, 1983

[30] Foreign Application Priority Data

Jul. 30, 1982 [JP] Japan .............................. 57-134106
Jul. 30, 1982 [JP] Japan .............................. 57-134109

[51] Int. Cl.³ ..................... C07C 50/36; C07C 167/02
[52] U.S. Cl. ................... 260/351.1; 260/365; 260/376; 549/336; 568/660
[58] Field of Search ................... 260/376, 351.1, 365; 549/336; 568/660

[56] References Cited

U.S. PATENT DOCUMENTS 3,427,327  2/1969  Chang .............................. 568/660
3,506,693  4/1970  Bucourt et al. .................. 549/336
4,116,981  9/1978  Kende ............................. 260/376

OTHER PUBLICATIONS

Neuman, *Tetrahedron Letters*, No. 20, 1978, pp. 1709–1712, "Photochemistry of Phenyl Alkyl Ketones Under Pressure".
Plattner et al., *Jol. of the American Chem. Soc.*, vol. 93, 1971, pp. 1758–1761, "The Synthesis of d & l-Sirenin and Their Absolute Configurations".
Rubin et al., *Jol. of Amer. Chem. Soc.*, vol. 74, 1952, pp. 425–428, "Synthesis of the Optically Active Enantiomorphic 2,3-Butanediols".
Carmack et al., *Jol. of Organic Chem.*, vol. 33, 1968, pp. 2171–2174, "The Synthesis of the Optically Active Cleland Reagent[(−)-1,4-Dithio-L$_g$-threitol].

*Primary Examiner*—Glennon H. Hollrah
*Assistant Examiner*—Raymond Covington
*Attorney, Agent, or Firm*—Birch, Stewart, Kolasch & Birch

[57] ABSTRACT

A process for preparing optically active 4-demethoxy-7-deoxydaunomycinone which comprises reacting a racemic mixture of the α-hydroxyketone of the formula:

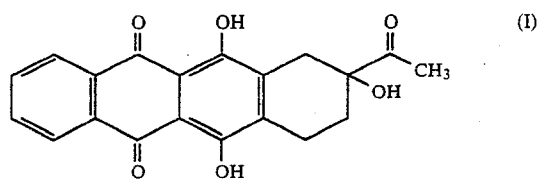

with an optical isomer of the α-glycol of the formula:

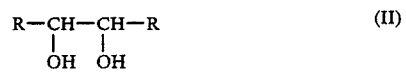

wherein R is a group of the formula:

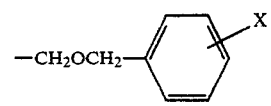

and X is a halogen atom or a lower alkyl group to give a diastereomeric mixture of the acetal of the formula:

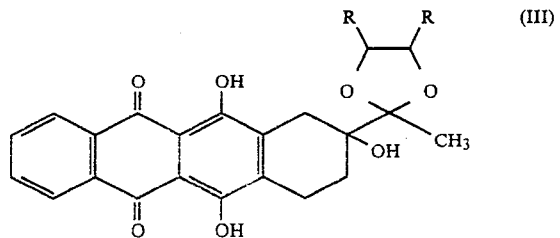

11 Claims, No Drawings

PREPARATION OF OPTICALLY ACTIVE 4-DEMETHOXYDAUNOMYCINONE

The present invention relates to preparation of optically active 4-demethoxydaunomycinone. More particularly, it relates to preparation of optically active 4-demethoxy-7-deoxydaunomycinone using a certain specific α-glycol as a resolving agent.

In one aspect of the invention, it pertains to optical resolution of a racemate of the α-hydroxyketone of the formula:

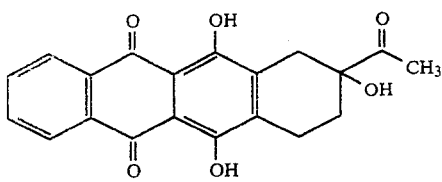
(I)

by the use of an optical isomer of the α-glycol of the formula:

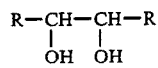
(II)

wherein R is a group of the formula:

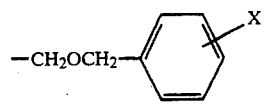

and X is a halogen atom such as chlorine, bromine or fluorine, preferably chlorine, or a lower alkyl group such as methyl, ethyl, propyl or isopropyl, preferably methyl, as the resolving agent. Namely, it is concerned with a process for optical resolution which comprises reacting a racemate of the α-hydroxyketone (I) with an optical isomer of the α-glycol (II) to give a diastereomeric mixture of the acetal of the formula:

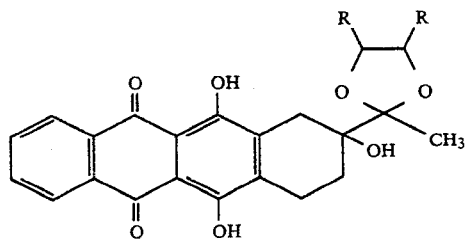
(III)

wherein two R groups take a trans configuration, separating the diastereomeric mixture into each of the diastereomers of the formulas:

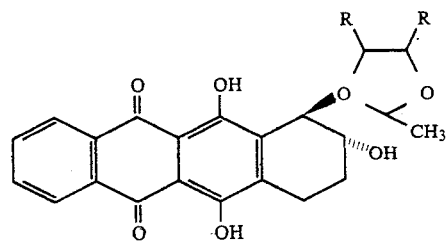
(III-A)

and

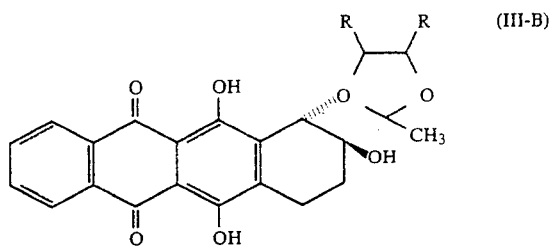
(III-B)

wherein R is as defined above and two R groups take a trans configuration and subjecting either one of the resultant diastereomer to deacetalization to give the corresponding optically active 4-demethoxy-7-deoxydaunomycinone of either one of the formulas:

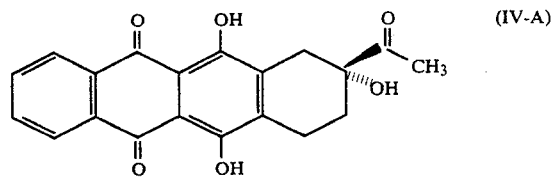
(IV-A)

and

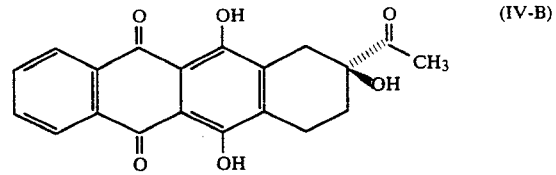
(IV-B)

In another aspect of the invention, it pertains to racemization of the optically active α-hydroxyketone of either one of the formulas (IV-A) and (IV-B) through the corresponding methylated product. Namely, it is concerned with a process for racemization which comprises methylating the optically active α-hydroxyketone (IV-A) or (IV-B) to give the corresponding methylated product of either one of the formulas:

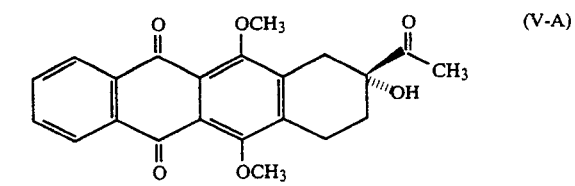
(V-A)

and

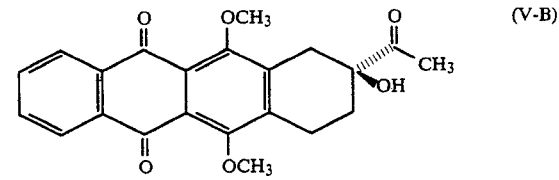
(V-B)

and reacting the latter with an acid to give a racemate of the α-hydroxyketone (I).

The α-glycol of the formula (II) as the resolving agent covers two optically active isomers which are representable by the formulas:

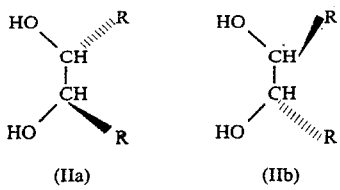

wherein R is as defined above. The asymmetric carbon atoms take the (R,R) configuration in the isomer (IIa) and the (S,S) configuration in the isomer (IIb).

When the α-glycol (IIa) is used as the resolving agent, the diastereomeric mixture comprises the following two acetals:

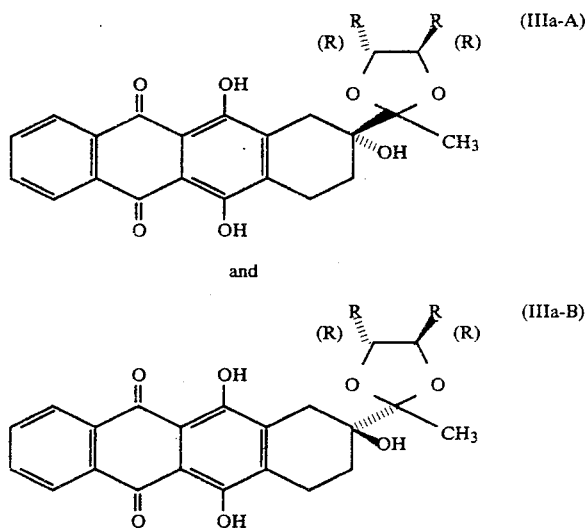

wherein R is as defined above. When the α-glycol (IIb) is used as the resolving agent, the diastereomeric mixture comprises the following two acetals:

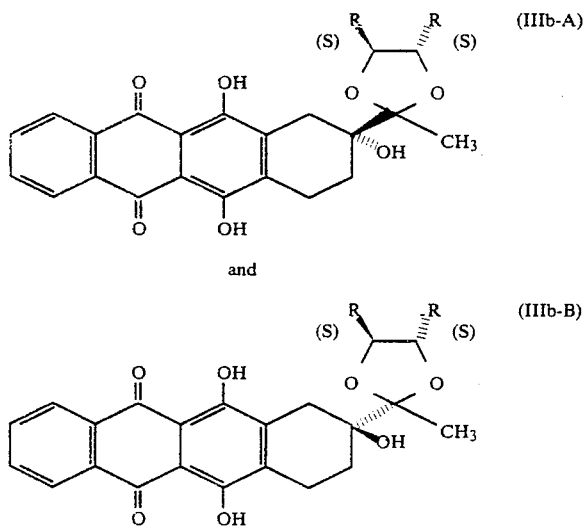

wherein R is as defined above.

The optically active 4-demethoxy-7-deoxydaunomycinone of the formula (IV-A) is useful as an intermediate in the synthesis of 4-demethoxydaunorubicin, which is known as an anthracycline antibiotic having a potent anti-tumor activity. For instance, the optically active 4-demethoxy-7-deoxydaunomycinone (IV-A) is converted into the optically active 4-demethoxydaunomycinone of the formula:

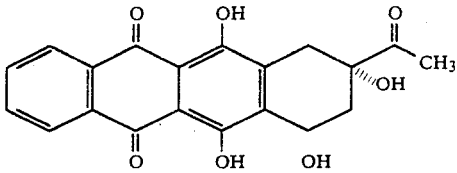

according to the procedure as described in Arcamone et al.: Experientia, 34, 1255 (1978) and condensing the latter with daunosamine to give 4-demethoxydaunorubicin.

The present invention has characteristic features not only in the optical resolution but also in the racemization, and these two will be hereinafter explained in detail.

Optical resolution

For preparation of the optically active 4-demethoxy-7-deoxydaunomycinone (IV-A), there are known two procedures as respectively disclosed in F. Arcamone et al.: Experientia, 34, 1255 (1978) and German Offenlegungsschrift No. 2,601,785.

In the latter procedure, an optically active compound of the formula:

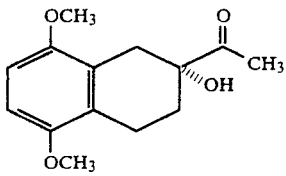

and phthalic anhydride are subjected to Friedel-Crafts reaction to give the 4-demethoxy-7-deoxydaunomycinone (IV-A). In this reaction, the racemization proceeds always to a certain extent, and therefore the product is optically impure. The purification of such an optically impure product to an optically pure one is accompanied with a great difficulty. Thus, the development of any advantageous procedure for optical resolution of a racemate of the α-hydroxyketone (I) (i.e. a mixture of the 4-demethoxy-7-deoxydaunomycinones (IV-A) and (IV-B)) is essential for industrial adoption of the above procedure.

Typical examples of the conventional procedures for optical resolution utilizing the ketonic functional group are as follows:

Procedure (a):

The procedure wherein a ketone is reacted with an optically active hydroxylamine to give the oxime, which is then subjected to optical resolution [R. Pappo et al.: Tetrahedron Lett., 1827 (1978)].

Procedure (b):

The procedure wherein a ketone is reacted with an optically active hydrazine to give the hydrazone, which is then subjected to optical resolution [W. N. Speckamp et al.: Rec. Trav. Chim., 91, 861 (1972)].

Procedure (c):

The procedure wherein a ketone is reacted with an optically active amine to give the imine, which is then subjected to optical resolution [F. Arcamone et al.: German Offenlegungsschrift No. 2,601,728].

Procedure (d):

The procedure wherein a ketone is reacted with an optically active α-aminoalcohol to give the oxazolidine, which is then subjected to optical resolution [R. Kelly et al.: Tetrahedron Lett., 1709 (1978)].

Procedure (e):

The procedure wherein a ketone is reacted with an optically active α-glycol to give the acetal, which is then subjected to optical resolution [E. J. Corey et al.: Chem. & Ind., 1664 (1961); M. Sanz-Burata et al.: Afinidad, 27, 693, 698, 705 (1970); H. Rapoport et al.: J. Am. Chem. Soc., 93, 1758 (1971)].

Procedure (f):

The procedure wherein a ketone is reacted with an optically active α-dithiol to give the thioacetal, which is then subjected to optical resolution [E. J. Corey et al.: J. Am. Chem. Soc., 84, 2938 (1962)].

Among them, the procedures (a), (b) and (c) may afford syn- and anti-isomers when the ketone is converted into its corresponding derivative. In the procedure (d), an additional asymmetric center is produced when the ketone is converted into the oxazolidine. Summarizing above, the procedures (a) to (d) have theoretically a possibility of producing more than two kinds of diastereomers, which naturally makes it very difficult to separate their mixture into each diastereomer.

Accordingly, a resolving agent effectively usable for optical resolution of a compound having a ketonic functional group is required to produce only two kinds of diastereomers. In addition, it is necessary that such a resolving agent meet the following requirements for industrial application: (1) it can be synthesized in fewer steps from a starting material of low cost; and (2) either one of two enantiomers can be readily available. Of these two requirements, the latter is practically important, because the choice of an appropriate enantiomer makes it possible to adopt a condition suitable for optical resolution. Usually, only one kind of enantiomer can be isolated in a pure state with a high yield.

As a result of the extensive study, it has been found that the optical isomer of the α-glycol (II) is a quite excellent resolving agent for a racemate of the α-hydroxyketone (I). Since the α-glycol (II) has a symmetric structure, there are produced only two kinds of diastereomers as the result of the reaction between the α-hydroxyketone (I) and the optical isomer of the α-glycol (II). Further, the optical isomer of the α-glycol (II) can be readily produced from mannitol or tartaric acid in a good yield. Moreover, separation of the diastereomeric mixture of the acetal produced from the α-hydroxyketone (I) and the α-glycol (II) into each diastereomer can be accomplished solely by crystallization. This is quite advantageous from the industrial viewpoint, because conventional optical resolution procedures using α-glycols have always required the use of gas chromatography for separation and recovery of each diastereomer.

The optically active α-glycol (IIa) or (IIb) to be used as the resolving agent in this invention can be produced from the corresponding optically active α-diol of either one of the formulas:

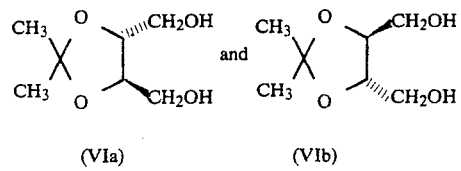

which may be prepared according to the procedure as described in H. O. L. Fisher et al.: J.Am.Chem.Soc., 74, 425 (1952); A. H. Haines et al.: J.Chem.Soc. Perkin Trans, I, 273 (1972); P. W. Feit, J.Med.Chem., 7, 14 (1964); M. Carmack et al., J.Org.Chem., 33, 2171 (1968), etc., by reacting the latter with a substituted benzyl chloride to give the corresponding optically active ether of either one of the formulas:

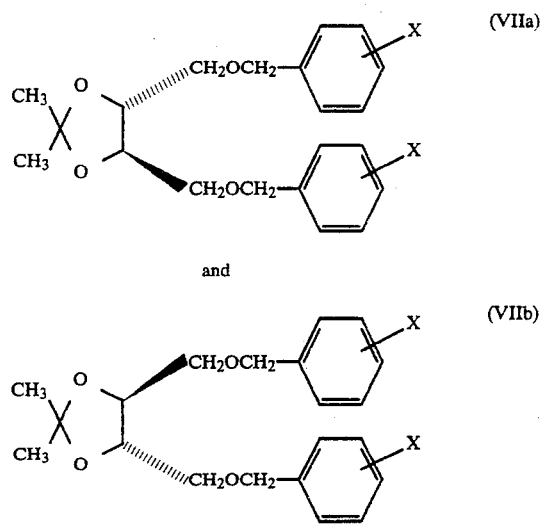

wherein X is as defined above, and subjecting the thus obtained ether (VIIa) or (VIIb) to deacetalization.

Namely, the conversion of the diol (VIa) or (VIb) into the ether (VIIa) or (VIIb) may be achieved by reacting the former with a substituted benzyl chloride in the presence of a base at room temperature or while heating. As the base, there may be employed sodium amide, triethylamine, potassium carbonate, sodium hydroxide, barium oxide, silver oxide, sodium hydride, etc. Among them, the use of sodium hydride is particularly preferred. The reaction is normally carried out in an inert solvent (e.g. dimethylsulfoxide, dimethylformamide, dimethoxyethane, tetrahydrofuran). The subsequent deacetalization of the ether (VIIa) or (VIIb) to the α-glycol (IIa) or (IIb) may be accomplished by treatment of the former with an acid (e.g. hydrochloric acid, sulfuric acid, p-toluenesulfonic acid, boron trifluoride-etherate), usually in an inert solvent (e.g. methanol, acetone, dioxane, tetrahydrofuran, water) at room temperature or while heating. These conversion and deacetalization procedures are per se known [Y. Inoue et al.: Synthesis, 688 (1978)].

The production of the optically active α-hydroxyketone (IV-A) or (IV-B) from their racemate (I) by the use of the optically active α-glycol (IIa) or (IIb) as the resolving agent may be performed in the following manner. Acetalization of the racemate (I) can be accomplished in a per se conventional procedure, e.g. by treatment with a slightly excessive amount of the optically active α-glycol (IIa) or (IIb) in the presence of a catalytic amount of an acid in a hydrocarbon solvent while azeotropically eliminating the by-produced water. Examples of the acid are hydrogen chloride, hydrogen bromide, sulfuric acid, p-toluenesulfonic acid, boron trifluoride-etherate, phosphoric acid, ion exchange resin, etc. Among them, the use of p-toluenesulfonic acid is especially preferred. Examples of the hydrocarbon solvent are benzene, toluene, etc.

Separation of the thus produced diastereomeric mixture into each diastereomer may be carried out, for instance, by distilling out the solvent from the reaction mixture and admixing the residue with ether or the like while stirring, whereby the optically active acetal (IIIa-A) or (IIIb-B) is predominantly crystallized. When desired, the product may be further subjected to recrystallization for enhancing the optical purification. The mother liquor after the separation of the optically active acetal (IIIa-A) or (IIIb-B) as above may be concentrated, followed by crystallization of the residue from ether or the like to give the other diastereomer (IIIa-B) or (IIIb-A).

The above obtained diastereomer (III-A) (i.e. (IIIa-A) or (IIIb-A)) is then subjected to deacetalization, i.e. acetal exchange or acid hydrolysis, whereby the optically active α-hydroxyketone (IV-A) is obtained. Likewise, deacetalization of the diastereomer (III-B) (i.e. (IIIa-B) or (IIIb-B)) gives the optically active α-hydroxyketone (IV-B), which is the enantiomer of the optically active α-hydroxyketone (IV-A). The said deacetalization is usually effected in the presence of an acid (e.g. hydrochloric acid, sulfuric acid, p-toluenesulfonic acid, boron trifluoride-etherate) in an inert solvent (e.g. methanol, acetone, dioxane, tetrahydrofuran, water) at room temperature or while heating.

As a result of the deacetalization, the optically active α-glycol (II) is liberated. It is readily recovered by a per se conventional procedure and can again be utilized as the resolving agent.

The subject matter relating to the "optical resolution" as explained above is the invention of S. Terashima, K. Tamoto and M. Sugimori and corresponds to Japanese Patent Application Nos. 134106/82 and 134109/82.

Racemization

After the desired optical isomer is recovered by the above optical resolution, there remains the other enantiomer in an yield of up to 50%. In order to enhance the efficiency of the above optical resolution, it is desirable to racemize such other enantiomer to obtain its racemate, which is again subjected to optical resolution as above. In general, however, racemization on the quaternary carbon atom as in the α-hydroxyketone (IV-A) or (IV-B) is extremely difficult or impossible.

As a result of extensive study, it has been found that the optically active α-hydroxyketone (IV-A) or (IV-B) can be readily racemized when once converted into the methylated compound (V-A) or (V-B). Thus, in this invention, the optically active α-hydroxyketone (IV-A) or (IV-B) is first converted into the corresponding methylated compound (V-A) or (V-B), which is then treated with an acid for racemization as well as demethylation.

The methylation of the optically active α-hydroxyketone (IV-A) or (IV-B) may be performed by a per se conventional procedure, e.g. treatment with dimethyl sulfate-anhydrous potassium carbonate-acetone or methyl iodide-anhydrous potassium carbonate-acetone.

The subsequent racemization is usually carried out in an inert solvent (e.g. water, acetic acid, trifluoroacetic acid) in the presence of an acid such as a sulfonic acid (e.g. p-toluenesulfonic acid, trifluoromethanesulfonic acid), hydrochloric acid or trifluoroacetic acids, preferably at a temperature of 90° to 120° C. Among the acid, the use of p-toluenesulfonic acid is favorable. The amount of the acid may be greatly excessive, e.g. from 50 to 100 times molar amount (preferably from 65 to 75 times molar amount, more preferably around 70 times molar amount), to the methylated compound (V-A) or (V-B).

As understood from the above, the present invention can provide the α-hydroxyketone (IV-A) in a high optical purity so that the production of optically active 4-demethoxydaunomycinone is facilitated. Since the unnecessary enantiomer as by-produced can be readily converted into the racemate and used again as the starting material for optical resolution, the efficiency of the production of 4-demethoxydaunomycinone is enhanced. In addition, it is advantageous that the recovery of the α-glycol (II) as the resolving agent can be accomplished by a simple operation with ease.

The subject matter relating to the "racemization" as explained above is the invention of S. Terashima, K. Tamoto and K. Koga and corresponds to Japanese Patent Application No. 33650/82.

Practical and presently preferred embodiments of the invention are illustratively shown in the following Examples wherein % is by weight unless otherwise indicated.

EXAMPLE 1

(1) To 50% sodium hydride (1.96 g) washed with dry n-hexane was added tetrahydrofuran (20 ml), and a solution of (R,R)(−)-2,3,-O-isopropylidene-threitol (VIa) ($[\alpha]_D^{20} = -4.2°$ (c=5.31 in CHCl$_3$); 3 g) in tetrahydrofuran (6 ml) was dropwise added thereto below 5° C. in 15 minutes, followed by elevation of the temperature to room temperature in 30 minutes. A solution of p-chlorobenzyl chloride (8.94 g) in tetrahydrofuran (15 ml) was dropwise added to the reaction mixture in 15 minutes, and the temperature was kept at 50° C. for 3 hours while stirring. After being allowed to cool, water and benzene were added to the mixture, followed by shaking. The extracted organic layer was washed with water, 5% hydrochloric acid, water, saturated sodium bicarbonate solution and water in order and dried. After removal of the solvent, the residue was subjected to column chromatography on silica gel (100 g) using benzene as an eluent to give 6.54 g of (R,R)(+)-1-O,4-O-bis(p-chlorobenzyl)-2,3-O-isopropylidene-threitol (VIIa: X=p-Cl) in 86% yield. $[\alpha]_D^{20} = +8.1°$ (c=6.17, CHCl$_3$). Mass spectrum (M+): 410.

(2) The thus obtained compound (VIIa: X=p-Cl) (4.5 g) was dissolved in a mixture of tetrahydrofuran (7.7 ml) and dioxane (12.4 ml), conc. hydrochloric acid (1 ml) was added thereto and the resulting mixture was stirred at 60° C. for 6 hours. After being allowed to cool, finely pulverized potassium carbonate (4.5 g) was portionwise added thereto while stirring. The resultant mixture was filtered, and the solvent was removed. The residue was purified by column chromatography on silica gel (50 g) using dichloromethane as an eluent to give 3.78 g of (R,R)-1-O,4-O-bis(p-chlorobenzyl)threitol (IIa: X=p-Cl) in 93% yield. M.P., 76°-78° C.

$[\alpha]_D^{20} = +6.3°$ (c=3.08, CHCl$_3$). Mass spectrum (M+): 370.

EXAMPLE 2

In the same manner as in Example 1, there was obtained (S,S)-1-0,4-0-bis(p-chlorobenzyl)threitol (IIb: X=p-Cl). M.P., 74°-77° C. $[\alpha]_D^{20} = -6.5°$ (c=3.01, CHCl$_3$). Mass spectrum (M+): 370.

EXAMPLES 3 TO 8

In the same manner as in Example 1, the compounds as shown in Tables 1 and 2 were obtained.

TABLE 1

| Example No. | X | Compound (VIIa) $[\alpha]_D^{20}$ (CHCl$_3$) | Compound (II-a) M.P. (°C.) | $[\alpha]_D^{20}$ (CHCl$_3$) |
|---|---|---|---|---|
| 3 | p-F | +5.9° (c = 5.61) | 71-72 | +4.8° (c = 3.02) |
| 4 | p-Br | +6.8° (c = 5.51) | 70-71 | +5.2° (c = 3.11) |
| 5 | p-CH$_3$ | +8.1° (c = 5.50) | 67-68 | +6.3° (c = 3.08) |

TABLE 2

| Example No. | X | Compound (VIIb) $[\alpha]_D^{20}$ (CHCl$_3$) | Compound (II-b) M.P. (°C.) | $[\alpha]_D^{20}$ (CHCl$_3$) |
|---|---|---|---|---|
| 6 | p-F | −6.1° (c = 5.69) | 70-71 | −4.9° (c = 2.95) |
| 7 | p-Br | −7.0° (c = 5.74) | 71-72 | −5.1° (c = 3.06) |
| 8 | p-CH$_3$ | −8.1° (c = 5.89) | 67-68 | −6.6° (c = 2.96) |

EXAMPLE 9

(1) A suspension of the racemic α-hydroxyketone (I) (mp., 214°-216° C.; 2.5 g), the optically active α-glycol (IIa: X=p-Cl) (3.03 g) and p-toluenesulfonic acid (81 mg) in benzene (100 ml) was heated under reflux for 13 hours while distilling out by-produced water azeotropically. The resultant mixture was allowed to cool to room temperature, dichloromethane (100 ml) and finely pulverized potassium carbonate (5 g) were added thereto and stirring was continued for 1 hour, followed by filtration. After removal of the solvent, the residue was purified by chromatography on silica gel (100 g) using a mixture of benzene and dichloromethane (1:1) as an eluent to give 5.2 g of a mixture of the acetal (IIIa-A: X=p-Cl) and (IIIa-B: X=p-Cl). $[\alpha]_D^{20} = +4.8°$ (c=0.65, CHCl$_3$). To the thus obtained product was added ether (200 ml), and a small amount of crystal seeds were added thereto. The resulting mixture was stirred for 15 hours. The precipitated crystals were collected by filtration, washed with a small quantity of cold ether and dried. Yield, 2.354 g (47%). M.P., 132°-136° C.

The precipitated crystals were recrystallized twice from acetonitrile to give the acetal (IIIa-A: X=p-Cl). Yield, 1.746 g (35%). M.P., 141°-142° C. $[\alpha]_D^{20} = -53.6°$ (c=0.50, CHCl$_3$).

Recrystallization again from acetonitrile showed the following physical properties:
M.P. = 141.5°-142° C.
$[\alpha]_D^{20} = -53.6°$ (c=0.51, CHCl$_3$).

Elementary analysis: Calcd. for C$_{38}$H$_{34}$Cl$_2$O$_9$: C, 64.69%; H, 4.86%. Found: C, 64.42%; H, 4.90%.

Separately, the filtrates after ether treatment were combined, distilled off (yield, 4.266 g; 49%) and recrystallized thrice from ether to give the acetal (IIIa-B: X=p-Cl). Yield, 0.925 g (18%). M.P., 120°-121° C. $[\alpha]_D^{20} = +66.5°$ (c=0.50, CHCl$_3$).

Recrystallization again from ether showed the following physical properties:
M.P. = 120°-121° C.
$[\alpha]_D^{20} = +66.8°$ (c=0.51, CHCl$_3$).

Elementary analysis: Calcd. for C$_{38}$H$_{34}$Cl$_2$O$_9$: C, 64.69%; H, 4.86%. Found: C, 64.52%; H, 4.83%.

(2-1) The acetal (IIIa-A: X=p-Cl) (200 mg) was dissolved in acetone (200 ml), and BF$_3$.Et$_2$O (0.18 ml) was added thereto. The resulting mixture was heated under reflux for 13 hours. After being allowed to cool, saturated sodium bicarbonate solution was added to the mixture, which was then extracted with chloroform. The organic layer was washed with water and dried. After removal of the solvent, the residue was purified by chromatography on silica gel (15 g) using a mixture of benzene and dichloromethane (3:1) as an eluent to give the crude product (97.8 mg; 98%). M.P., 214°-217° C. $[\alpha]_D^{20} = -81.9°$ (c=0.116, CHCl$_3$). Recrystallization of the product from benzene gave 80.1 mg of an optically active compound (IV-A) in 80% acid. M.P., 218°-219° C. $[\alpha]_D^{20} = -89.9°$ (c=0.102, CHCl$_3$). Elementary analysis: Calcd. for C$_{20}$H$_{16}$O$_6$: C, 68.18%; H, 4.58%. Found: C, 68.35%; H, 4.62%.

The ether (VIIa: X=p-Cl) obtained on purification by chromatography was further subjected to purification by thin layer chromatography (silica gel; eluent:-benzene) and short-path distillation under reduced pressure to give 81.6 mg (71.6%) of the acetal of the optionally active α-glycol having the following formula:

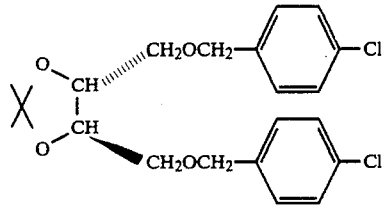

B.P.: 260° C. (bath temp.)/0.01-0.02 mmHg.

$[\alpha]_D^{20} = +7.8°$ (c=5.97, CHCl$_3$). (2-2) The acetal (IIIa-A: X=p-Cl) (100 mg) was dissolved in a mixture of tetrahydrofuran (2 ml) and dioxane (5 ml), and conc. hydrochloric acid (1 ml) was added thereto. The resulting mixture was heated under reflux for 2 hours. After allowed to cool, saturated sodium bicarbonate solution was added to the mixture, which was then extracted with chloroform. The organic layer was washed with water, dried and purified by chromatography on silica gel (7.5 g) using a mixture of benzene and dichloromethane (3:1) as an eluent to give the crude product (48.2 mg; 97%). M.P., 214°-218° C. $[\alpha]_D^{20} = -84.7°$ (c=0.118, CHCl$_3$). Recrystallization of the product from benzene gave 38.1 mg of the optically active compound (IV-A). M.P., 218°-219° C. $[\alpha]_D^{20} = -90.3°$ (c=0.106, CHCl$_3$).

The α-glycol (IIa: X=p-Cl) obtained on purification by chromatography was further subjected to purification by thin layer chromatography (silica gel; eluent: dichloromethane) to give 39.4 mg (75%) of the optically active α-glycol (IIa: X=p-Cl). M.P., 76°-78° C. $[\alpha]_D^{20} = +5.7°$ (c=2.98, CHCl$_3$).

EXAMPLE 10

(1) In the manner as in Example 9 (1), the racemic α-hydroxyketone (I) (500 mg) and the optically active α-glycol (IIb: X=p-Cl) (606 mg) were subjected to reaction. After being purified by chromatography, there was obtained 1021 mg of a mixture of the acetal (IIIb-A: X=p-Cl) and (IIIb-B: X=p-Cl). $[\alpha]_D^{20} = -5.4°$ (c=0.61, CHCl$_3$).

The thus obtained mixture was treated with ether, whereby 449 mg (45%) of crystals were precipitated. M.P., 133°–138° C. Recrystallization of the crystals from acetonitrile gave the acetal (IIIb-B: X=p-Cl). Yield, 387 mg (39%). M.P., 140.5°–141.5° C. $[\alpha]_D^{20} = +53.3°$ (c=0.59, CHCl$_3$).

Recrystallization again from acetonitrile showed the following physical properties:
M.P. = 141°–142° C.
$[\alpha]_D^{20} = +53.8°$ (c=0.55, CHCl$_3$).

Elementary analysis: Calcd. for C$_{38}$H$_{34}$Cl$_2$O$_9$: C, 64.69%; H, 4.86%. Found: C, 64.76%; H, 4.74%.

Separately, the filtrates after ether treatment were concentrated (yield, 500 mg; 50%) and recrystallized twice from ether to give the acetal (IIIb-A: X=p-Cl). Yield, 213 mg (21%). M.P., 119.5°–120.5° C. $[\alpha]_D^{20} = -66.0°$ (c=0.57, CHCl$_3$).

Recrystallization again from ether showed the following physical properties:
M.P. = 120°–121° C.
$[\alpha]_D^{20} = -66.4°$ (c=0.53, CHCl$_3$).

Elementary analysis: Calcd. for C$_{38}$H$_{34}$Cl$_2$O$_9$: C, 64.69%; H, 4.86%. Found: C, 64.64%; H, 4.92%.

(2-1) In the same manner as in Example 9 (2-1), the acetal (IIIb-A: X=p-Cl) (100 mg) was subjected to reaction to obtain 49.0 mg (98%) of the crude product. M.P., 215°–217° C. $[\alpha]_D^{20} = -84.6°$ (c=0.112, CHCl$_3$). Recrystallization of the product from benzene gave 38.2 mg (76%) of the optically active compound (IV-A). M.P., 218°–219° C. $[\alpha]_D^{20} = -90.1°$ (c=0.108, CHCl$_3$).

(2-2) In the same manner as in Example 9 (2-2), the acetal (IIIb-A: X=p-Cl) (100 mg) was subjected to reaction to obtain 48.5 mg (97%) of the crude product. M.P., 215°–218° C. $[\alpha]_D^{20} = -83.2°$ (c=0.106, CHCl$_3$). Recrystallization of the product from benzene gave 38.4 mg (77%) of the optically active compound (IV-A). M.P., 218°–219° C. $[\alpha]_D^{20} = -90.0°$ (c=0.110, CHCl$_3$).

EXAMPLE 11

(1) In the same manner as in Example 9 (2-1), the acetal (IIIa-B: X=p-Cl) (100 mg) was subjected to reaction to obtain 48.4 mg (97%) of the crude product. M.P., 215°–217° C. $[\alpha]_D^{20} = +84.2°$ (c=0.106, CHCl$_3$). Recrystallization of the product from benzene gave 39.5 mg (79%) of the optically active compound (IV-B). M.P., 218°–220° C. $[\alpha]_D^{20} = +89.5°$ (c=0.102, CHCl$_3$).

Elementary analysis: Calcd. for C$_{20}$H$_{16}$O$_6$: C, 68.18%; H, 4.58%. Found: C, 67.90%; H, 4.53%.

(2) In the same manner as in Example 9 (2-1), the acetal (IIIb-B: X=p-Cl) (100 mg) was subjected to reaction to obtain 49.3 mg (99%) of the crude product. M.P., 215°–217° C. $[\alpha]_D^{20} = +83.7°$ (c=0.104, CHCl$_3$). Recrystallization of the product from benzene gave 39.1 mg (78%) of the optically active compound (IV-B). $[\alpha]_D^{20} = +89.8°$ (c=0.120, CHCl$_3$).

EXAMPLE 12

(1) 2-Acetyl-2,5,12-trihydroxy-1,2,3,4,6,11-hexahydronaphthacene-6,11-dione enriched in S-form (R:S=38:62) having a specific optical rotation of $[\alpha]_D^{20} = +21.6°$ (c=0.1, CHCl$_3$) (50 mg) was dissolved in anhydrous acetone (10 ml), anhydrous potassium carbonate (100 mg) and dimethyl sulfate (82 mg) were added thereto, and the resultant solution was heated under reflux for 12 hours. After completion of the reaction, the solid substance was separated by filtration and washed with acetone. The combined filtrate was concentrated under reduced pressure. The residue was dissolved in chloroform (30 ml), washed with water (20 ml×3) and saturated sodium chloride solution (20 ml), dried over anhydrous magnesium sulfate and filtered. The filtrate was distilled under reduced pressure to give 47 mg of 2-acetyl-5,12-dimethoxy-1,2,3,4,6,11-hexahydro-2-hydroxynaphthacene-6,12-dione having a specific optical rotation of $[\alpha]_D^{20} = +5.6°$ (c=1.15, CHCl$_3$).

(2) 2-Acetyl-5,12-dimethoxy-1,2,3,4,6,11-hexahydro-2-hydroxynaphthacene-6,11-dione enriched in S-form (R:S=38:62) having a specific optical rotation of $[\alpha]_D^{20} = +5.6$ (c=1.15, CHCl$_3$) (21 mg) was dissolved in a mixture of water (0.37 ml) and acetic acid (0.64 ml), p-toluenesulfonic acid (735 mg) was added thereto, and the resulting solution was heated at 110° C. for 20 hours. After being cooled, the reaction mixture was diluted with water and extracted with dichloromethane. The extract was washed with aqueous sodium bicarbonate solution and water, and dried over anhydrous magnesium sulfate. After removal of the solvent, the residue was purified by thin layer chromatography on silica gel using a mixture of benzene and ethyl acetate (8:1) as an eluent to give 16 mg of the racemic compound. M.P., 212°–215° C. $[\alpha]_D^{20} = +0.6°$ (c=0.11, CHCl$_3$).

What is claimed is:

1. A process for preparing optically active 4-demethoxy-7-deoxydaunomycinone which comprises reacting a racemate of the α-hydroxyketone of the formula:

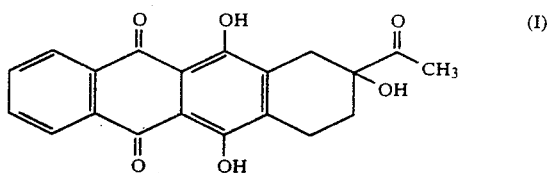

with an optical isomer of the α-glycol of the formula:

wherein R is a group of the formula:

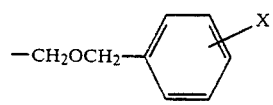

and X is a halogen atom of a layer alkyl group in the presence of a catalytic amount of an acid to give a diastereomeric mixture of the acetal of the formula:

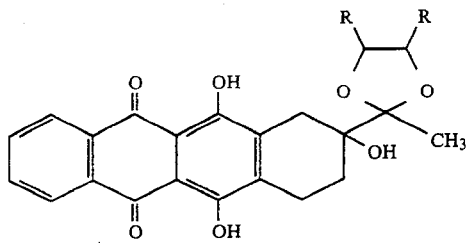

wherein two R groups take a trans configuration, separating the diastereomeric mixture into each of the diastereomers of the formulas:

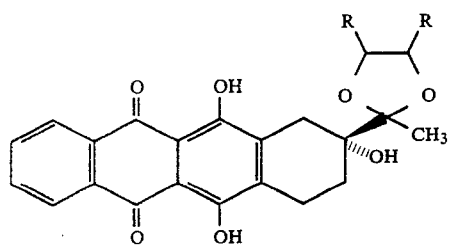

and

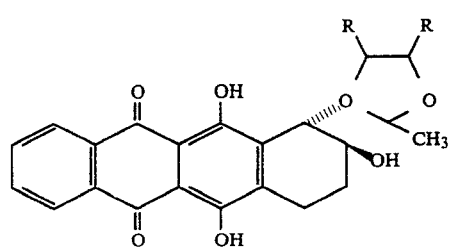

wherein R is as defined above and two R groups take a trans configuration by precipitation from a solvent to which said diastereomers show different solubilities and subjecting either one of the resultant diastereomer to deacetalization by treatment with an acid to give the corresponding optically active 4-demethoxy-7-deoxydaunomycinone of either one of the formulas:

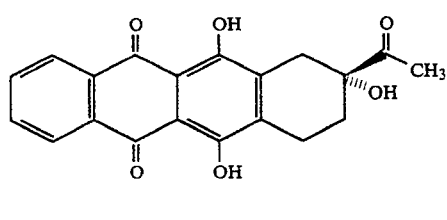

and

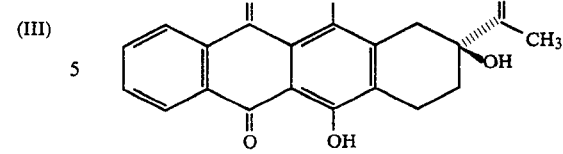

2. The process according to claim 1, wherein the α-glycol (II) is the one of the formulas:

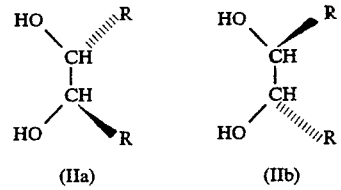

wherein R is as defined in claim 1.

3. The process according to claim 1, wherein X is a chlorine atom.

4. An optically active α-glycol of the formula:

wherein R is a group of the formula:

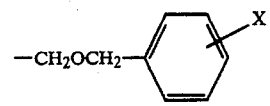

and X is a halogen atom or a lower alkyl group.

5. An optically active α-glycol according to claim 4, wherein X is a chlorine atom.

6. An optically active α-glycol according to claim 4, which is represented by the formula:

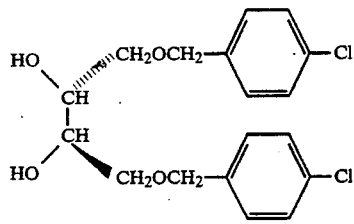

7. An optically active α-glycol according to claim 4, wherein X is a bromine atom.

8. An optically active α-glycol according to claim 4, wherein X is a methyl group.

9. A process according to claim 1, wherein said reaction of said racemate of the α-hydroxyketone (I) with acid α-glycol (II) is conducted in the presence of a catalytic amount of p-toluenesulfonic acid.

10. A process according to claim 1, wherein said solvent is an ether.

11. A process according to claim 1, wherein said acid utilized in said deacetalization step is a member selected from the group consisting of hydrochloric acid, sulfuric acid, p-toluenesulfonic acid and boron trifluoride-etherate.

* * * * *